United States Patent [19]
Baker et al.

[11] Patent Number: 5,665,097
[45] Date of Patent: Sep. 9, 1997

[54] CLIP APPLICATOR

[76] Inventors: John W. Baker, 4 Wachusett Dr., Acton, Mass. 01720; Jeffrey D. Baker, 5 Thistle La., Westford, Mass. 01886

[21] Appl. No.: 426,811

[22] Filed: Apr. 21, 1995

[51] Int. Cl.⁶ .................................................. A61B 17/00
[52] U.S. Cl. .......................... 606/143; 606/139; 227/901
[58] Field of Search ............................ 606/142, 143, 606/139, 151; 227/901

[56] References Cited

U.S. PATENT DOCUMENTS

| | | |
|---|---|---|
| 3,604,425 | 9/1971 | LeRoy . |
| 4,612,932 | 9/1986 | Caspar et al. . |
| 4,637,395 | 1/1987 | Caspar et al. ........................... 606/143 |
| 4,821,721 | 4/1989 | Chin et al. ............................... 606/143 |
| 4,854,317 | 8/1989 | Braun ...................................... 606/143 |
| 5,035,692 | 7/1991 | Lyon et al. .............................. 606/143 |
| 5,207,692 | 5/1993 | Kraus et al. ............................. 606/143 |

*Primary Examiner*—Jeffrey A. Schmidt
*Attorney, Agent, or Firm*—Pandiscio & Pandiscio

[57] ABSTRACT

A clip applicator adapted to apply and remove C-shaped scalp clips from a surgical incision site, wherein the clip applicator includes a body, a trigger and a lever mounted on the body and mutually operable between respective first and second positions relative to the body. The lever includes a clip-engaging portion disposed at a distal end thereof and a trigger-engaging portion disposed at a proximal end thereof. The lever is movable from the lever first position to the lever second position in response to the trigger moving from a trigger first position to a trigger second position. The clip applicator further includes a magazine that is releasably fastened to the body. The magazine is adapted to store a plurality of clips, and to serially dispense the clips from the magazine.

10 Claims, 13 Drawing Sheets

CLIP APPLICATOR

FIELD OF THE INVENTION

The present invention relates generally to clip applicators, and more particularly to magazine-fed, hand-held hemostatic clip applicators.

BACKGROUND OF THE INVENTION

In performing various surgical procedures on the head, it is often necessary for the surgeon to make lengthy incisions in the patient's scalp so as to expose the underlying anatomical structure. The free ends of the scalp tissue are generally clamped off during the surgery to minimize blood loss, and then the incisions are closed back up at the conclusion of the surgical procedure. Hemostatic clips for clamping off the tissue, and applicators for applying those clips to the scalp, are well known in the art.

For example, U.S. Pat. No. 3,604,425, issued to LeRoy, teaches a hemostatic clip in the form of a tubular body member having a longitudinal slit extending completely across the body. The slit is adapted to receive a wound flap when the tubular body is distended from its original shape. A pair of projections project outwardly from the body member along a longitudinal line disposed about 90° from the slit. These projections act as a convenient means for distending the body from its original shape when an external force is applied to the two projections. A pliers-type applicator is also taught in the patent to LeRoy. LeRoy, however, does not disclose any means for maintaining a plurality of his clips in position for ready application to an incision site.

U.S. Pat. Nos. 4,612,932 and 4,637,395, both issued to Casper et al., teach a scalp clip applicator and magazine system. The applicator is adapted to apply C-shaped scalp clips one after another to the skin flaps of an incision. The clip applicator and magazine system of Casper et al. alleviates the need to insert an individual scalp clip into the applicator after each preceding clip has been applied to the skin flaps. To this end, Casper et al. teach a magazine for holding a plurality of scalp clips one behind the other. The magazine arranges the free end of each scalp clip so that it rests against the bridge of its preceding scalp clip. In this way, the scalp clips are properly oriented within the magazine. The magazine guides the scalp clips as they are displaced toward an open end of the magazine by spring means. A stationary jaw is disposed at the open end of the magazine to help maintain the scalp clips within the magazine prior to their application to the incision site. When the magazine is assembled to the applicator, this stationary jaw is positioned in opposing relation to a movable jaw which is disposed on the applicator.

With the device of Casper et al., the magazine's stationary jaw and the applicator's movable jaw are initially arranged in a first position in which they are remote from one another. In this first position, the magazine's stationary jaw projects downwardly, and the applicator's movable jaw projects upwardly, with respect to the feed path of the scalp clips. In this way, as a leading portion of a scalp clip moves past the magazine's stationary jaw and the applicator's movable jaw, a trailing portion of the scalp clip engages both the magazine's stationary jaw and the applicator's movable jaw so as to halt forward movement of the scalp clip relative to the magazine. When the scalp clip is to be deployed, the applicator's movable jaw is brought closer to the magazine's stationary jaw so as to deform the trailing portion of the scalp clip. This in turn causes the leading portion of the scalp clip to expand so that the scalp clip may be applied to the incision site.

Unfortunately, the device disclosed in the Casper et al. patents can sometimes "spit" clips. In addition, the device disclosed in the Casper et al. patents cannot be used to remove deployed scalp clips at the conclusion of the surgical procedure.

U.S. Pat. No. 4,854,317, issued to Braun, teaches an applicator for C-shaped scalp clips, wherein the applicator comprises a stationary edge, a movable edge, and a scalp clip retaining element. The movable edge of the applicator can be brought toward the stationary edge while the retaining element is fixed in its open position so as to apply a scalp clip to an incision site. When the direction of motion of the movable edge is reversed, the movable edge immediately causes the retaining element to assume its locked position.

Unfortunately, while the device disclosed in the Braun patent tends to prevent clip spitting, it is also relatively complex in construction. Furthermore, the device disclosed in the Braun patent cannot be used to remove a scalp clip at the conclusion of the surgical procedure.

OBJECTS OF THE INVENTION

Accordingly, one object of the present invention is to provide an improved clip applicator which is adapted to reliably deploy hemostatic clips while utilizing a relatively simple construction.

Another object of the present invention is to provide an improved clip applicator which is adapted to remove a scalp clip from the surgical site at the conclusion of the surgical procedure.

Still another object of the present invention is to provide an improved method for removing a scalp clip from the surgical site at the conclusion of the surgical procedure.

SUMMARY OF THE INVENTION

These and other objects of the present invention are achieved through the provision and use of a novel clip applicator that is adapted to apply and remove C-shaped scalp clips. The C-shaped scalp clips contemplated for use with the present invention comprise two legs joined by a resilient bridge, and include facing clamping jaws at their free ends. The bridge includes upper and lower ears adapted to urge the clamping jaws open in response to actuation of the novel clip applicator.

The clip applicator of the present invention includes a body comprising a trigger and a lever, both of which are movably fastened to the body. The trigger is operable between a trigger first position and a trigger second position relative to the body. The trigger is normally pivotally biased in its trigger first position by spring means. In a preferred embodiment, the trigger comprises (i) means for moving the trigger from its trigger first position to its trigger second position, and (ii) a lever-engaging portion.

The lever has a lever first position and a lever second position relative to the body. The lever is normally pivotally biased in its lever first position by spring means. In a preferred embodiment, the lever comprises an elongate beam having a clip-engaging portion disposed at a distal end thereof and a trigger-engaging portion disposed at a proximal end thereof. The lever is movable from the lever first position to the lever second position in response to the trigger moving from the trigger first position to the trigger second position. Advantageously, the trigger-engaging portion of the lever loosely engages the lever-engaging portion of the trigger such that the clip-engaging portion of the lever is movable relative to the body when the lever is in the lever first position.

The clip applicator of the present invention further includes a magazine that is releasably fastened to the body. The magazine is adapted to store a plurality of clips, and to serially dispense those clips from the magazine. The clips are stored in the magazine with their free ends resting against the bridge of an adjacent clip. The magazine comprises an open end toward which the free ends of the legs of the clips point. The magazine further comprises a tube having side walls, means for orienting the clips within the tube, means for releasably locking the clips within the tube, and a lip projecting into the open end of the tube. In the preferred embodiment, the lip is shaped so as to selectively engage the upper ear of each of the clips as the clip moves toward the open end of the tube. The magazine is positioned on the body so that the clip-engaging portion of the lever will engage the lower ear of each clip as the clip moves toward the open end of the tube. To dispense a clip at a surgical incision site, the clip-engaging portion of the lever is moved toward the lip by the trigger being moved from the trigger first position toward the trigger second position. Means for urging the clips toward the open end of the tube are also provided in the invention.

The clip applicator of the present invention is used to apply a clip to a surgical incision site by the following method. The clip applicator is first actuated so as to position the ears of a first clip adjacent to the clip-engaging portion of the lever and the lip of the magazine. The clamping jaws of the clip are then positioned so as to be adjacent to a surgical incision site. The trigger is then moved from the trigger first position to the trigger second position. In this way, the lever moves from the lever first position to the lever second position. As a result, the clip-engaging portion of the lever engages the lower ear of the clip while the lip engages the upper ear of the clip. Thus the clamping jaws are caused to spread apart so as to capture a portion of the tissue surrounding the surgical incision. The trigger is subsequently moved from the trigger second position to the trigger first position, thereby moving the lever from the lever second position to the lever first position. This movement causes the clip-engaging portion of the lever to disengage from the ears of the scalp clip, thus allowing the clamping jaws to grip the tissue surrounding the surgical incision and thereby to deploy the scalp clip. The loose engagement between the lever-engaging portion of the trigger and the trigger-engaging portion of the lever permit the clip applicator to be easily disengaged from the deployed clip.

To remove a previously deployed scalp clip, the clip applicator is positioned so that the clip-engaging portion of the lever is adjacent to the ears of the previously deployed scalp clip. The clip-engaging portion of the lever is then pressed against the lower ear of the deployed clip. This causes the clip-engaging portion of the lever to move relative to the body by an amount sufficient to re-capture the deployed clip between the clip-engaging portion of the lever and the lip of the magazine tube, while at the same time, the lever is maintained in the lever first position. The trigger is then moved from the trigger first position to the trigger second position. As a result, the lever moves from the lever first position to the lever second position whereby the clip-engaging portion of the lever engages the lower ear of the released clip while the lip engages the upper ear of the released clip. Thus the clip's clamping jaws are caused to once again spread apart so as to release the previously captured portion of the tissue surrounding the surgical incision.

BRIEF DESCRIPTION OF THE DRAWINGS

Still other objects and features of the present invention will be more fully disclosed or rendered obvious by the following detailed description of the preferred embodiment of the invention, which is to be considered together with the accompanying drawings wherein like numbers refer to like parts and further wherein.

DETAILED DESCRIPTION OF THE PREFERRED EMBODIMENT

Figure 1:
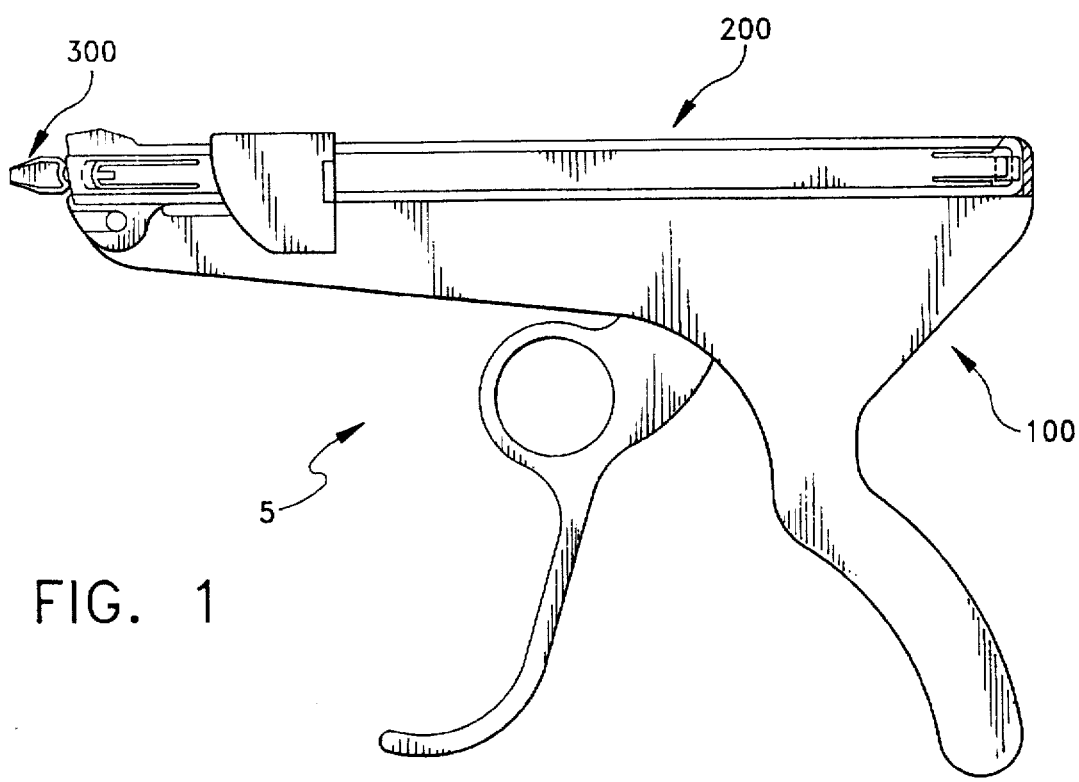
FIG. 1 is a side view of the clip applicator of the present invention.

Looking first at FIG. 1, the preferred embodiment of the present invention comprises a clip applicator 5 which generally comprises a pistol grip subassembly 100, a magazine subassembly 200, and a plurality of scalp clips 300.

Figure 2:
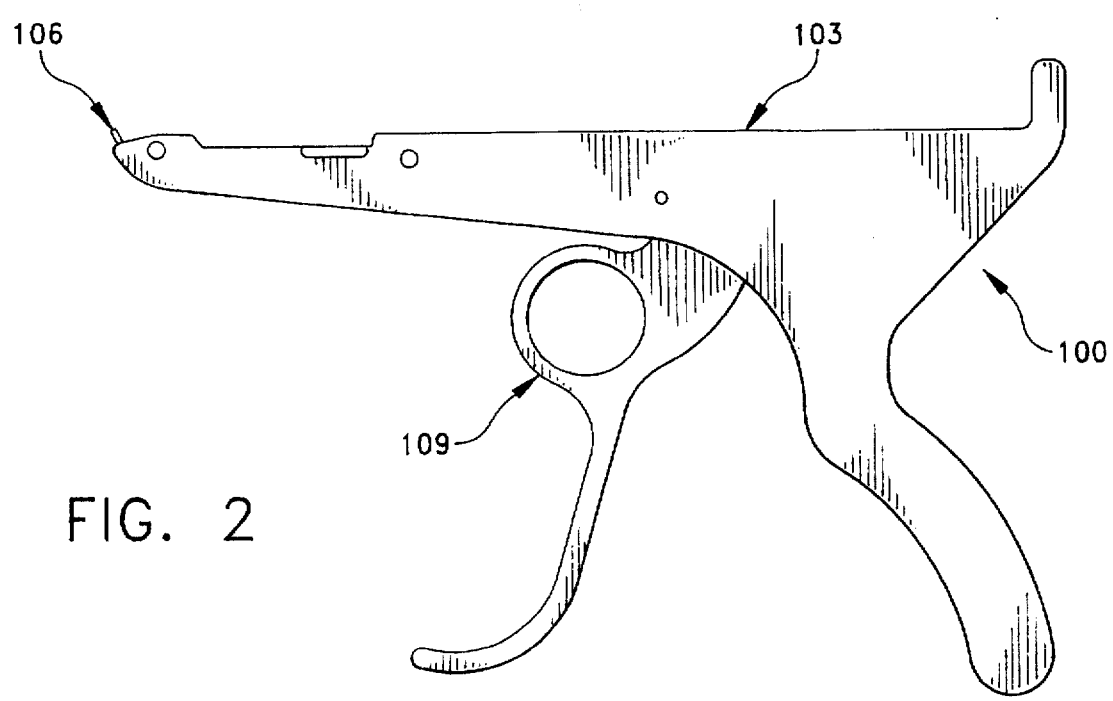
FIG. 2 is a side view of the clip applicator's pistol grip subassembly.
Figure 27:
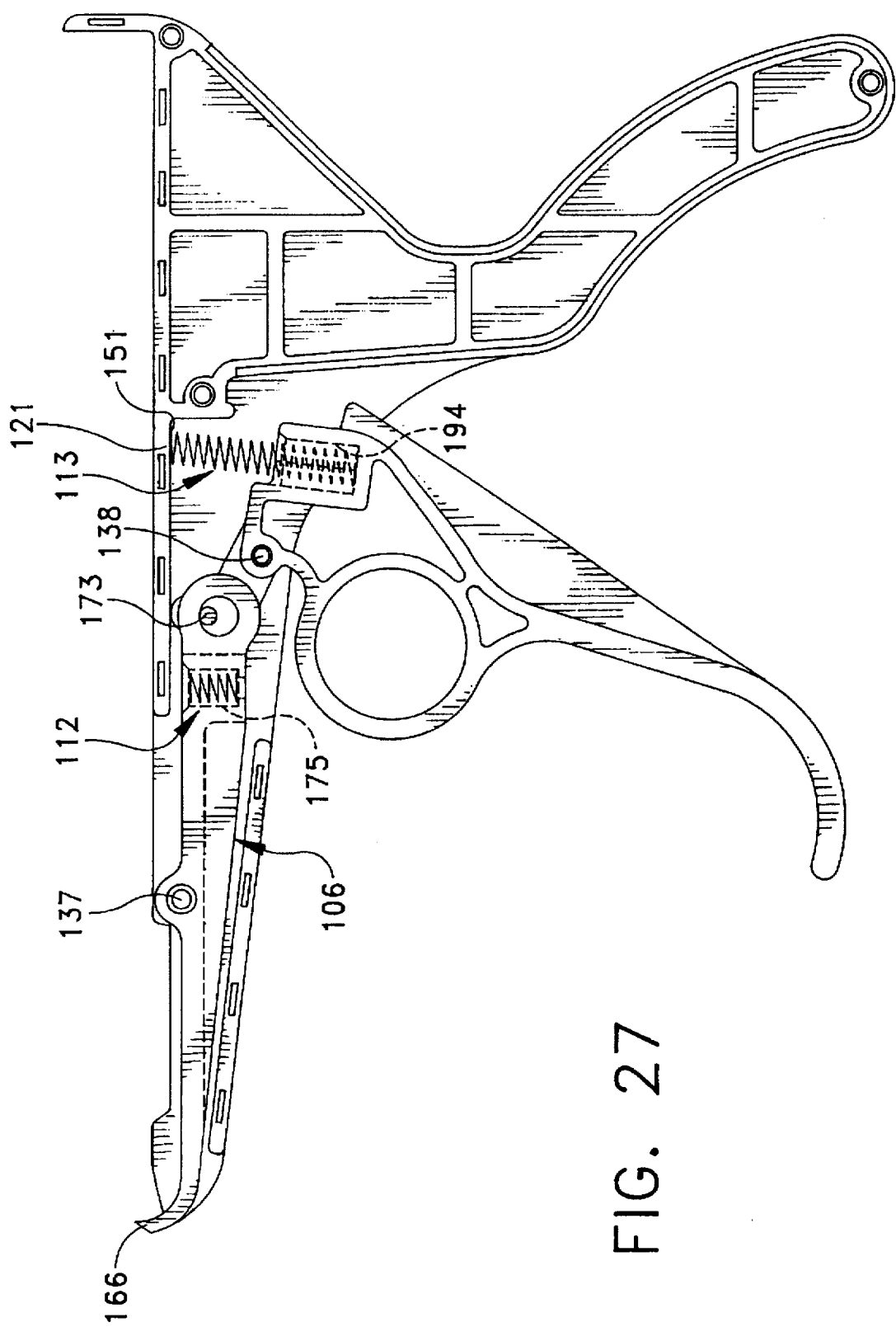
FIG. 27 is a side view of the pistol grip subassembly, shown with the left half of the body removed, and shown with the trigger in its normal, at rest position.
Figure 28:
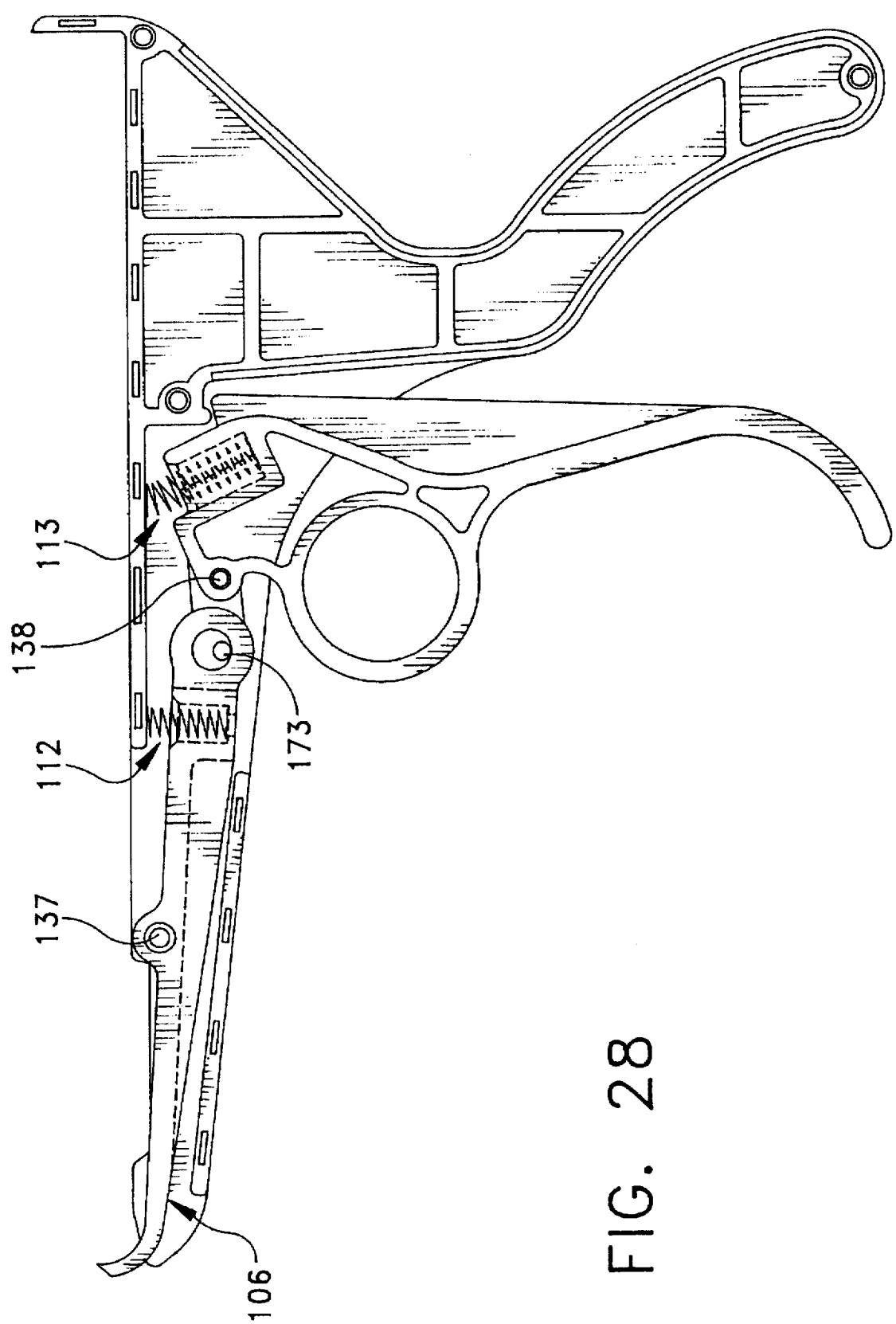
FIG. 28 is a view like that of FIG. 27, except that the trigger is shown in its activated position and the lever is shown in the position it would assume if it were opening a scalp clip with its distal end.
Figure 33:
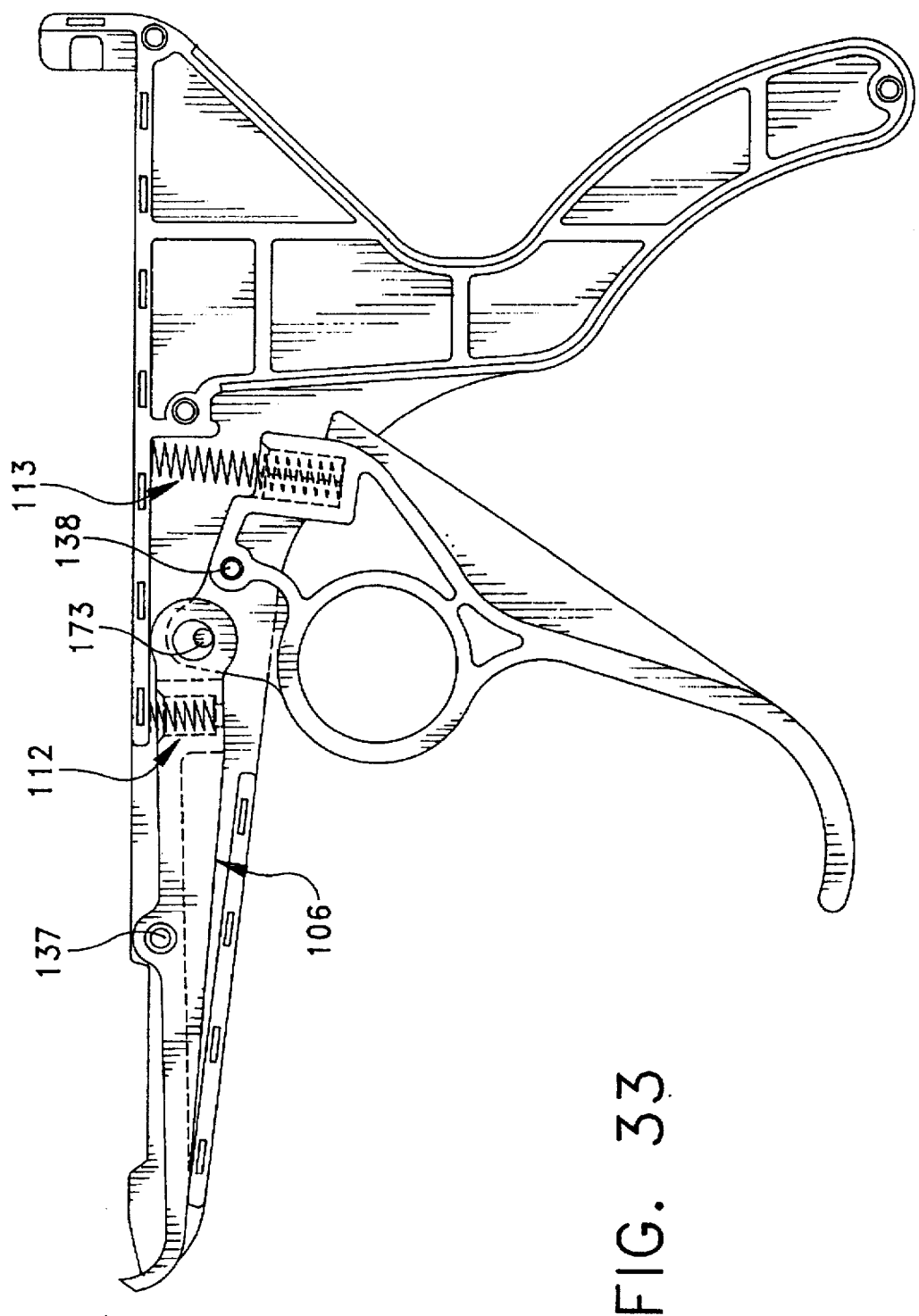
FIG. 33 is a view like that of FIG. 27, except that the lever is shown in the position it would assume if a downwardly-directed force was being applied to the lever's distal end.

Pistol grip subassembly 100 comprises a body 103 (FIG. 2), a lever 106 (FIGS. 2, 7, 8, 27, 28 and 33), a trigger 109 (FIG. 2), and a pair springs 112 and 113 (FIGS. 27, 28 and 33). In a preferred embodiment, pistol grip subassembly 100 may be formed from either a biocompatible polymer, a biocompatible metal, or both.

Referring now to FIGS. 2–6, body 103 is generally pistol-shaped, and preferably comprises two halves 103A, 103B so as to facilitate assembly of the component parts of pistol grip subassembly 100. More particularly, body 103 comprises a hand grip 115, an interior chamber 118, a top wall 121, a rear magazine retention channel 124, a pair of front magazine pivot tabs 127, and a pair of retainer slide tabs 130. Hand grip 115 is sized and shaped so as to accommodate a human hand in a manner similar to the handle of a gun.

Interior chamber 118 is generally defined by side walls 131A, 131B of body 103. Chamber 118 extends along a distal portion of body 103 and receives lever 106 and a portion of trigger 109, as will hereinafter be disclosed in further detail. Side walls 131A, 131B each comprise a shoulder 133A, 133B, respectively, and bores 134A, 134B and 135A, 135B, respectively. Side walls 131A, 131B also each comprise a plurality of blind holes 136A, 136B, respectively. Each shoulder 133 projects into chamber 118 so as to limit the movement of trigger 109, as will hereinafter be disclosed in further detail. Bores 134A, 134B and bores 135A, 135B extend completely through side walls 131A, 131B, respectively. Bores 134A, 134B are adapted to accept a lever pivot pin 137 (FIGS. 27, 28 and 33), and bores 135A, 135B are adapted to accept a trigger pivot pin 138 (FIGS. 27, 28 and 33). Bores 136A, 136B are adapted to accept appropriate fastening means for fastening the two body halves 103A, 103B together, as is well known in the art.

A bottom opening 139 (FIGS. 4 and 5) is defined by the lower portion of each side wall 131A, 131B when the two body halves 103A, 103B are assembled together. Bottom opening 139 is disposed in opposing relation to top wall 121. Bottom opening 139 is sized and shaped to permit a portion of trigger 109 to pivotally project out of the bottom side of body 103, as will hereinafter be disclosed in further detail.

Figure 4:
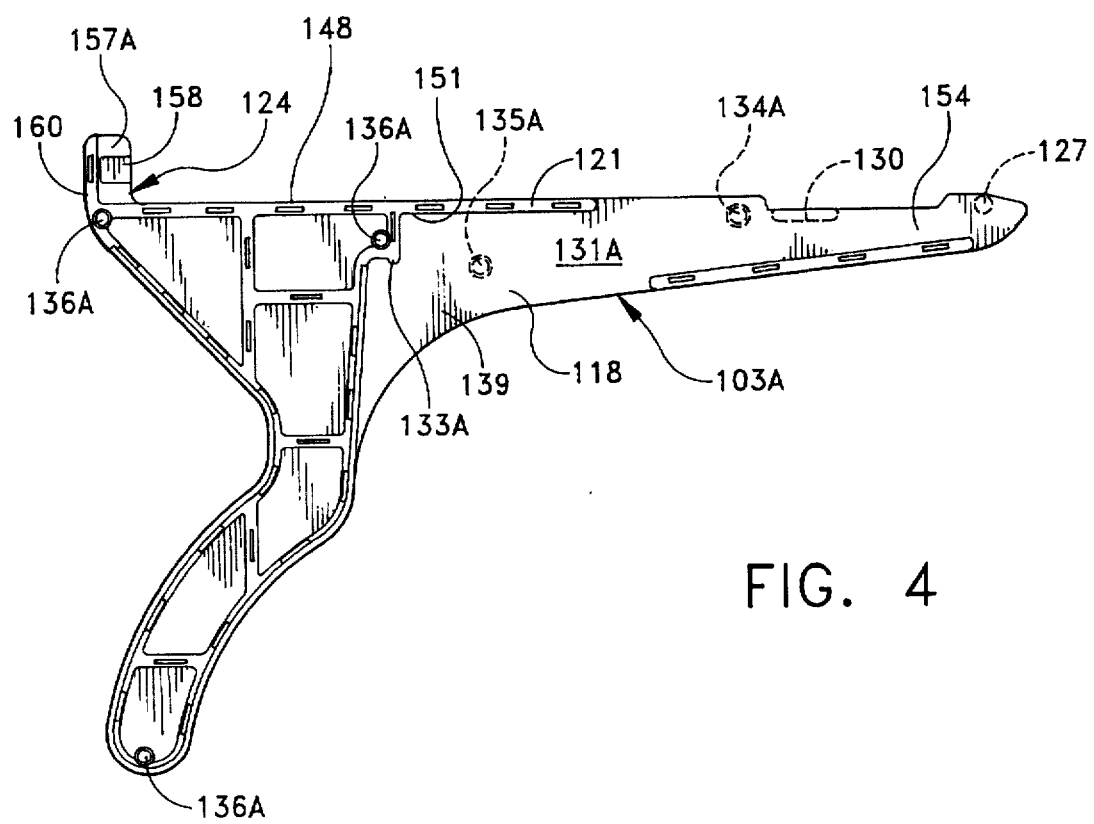
FIG. 4 is an internal side view of the left half of the body of the pistol grip subassembly.
Figure 5:
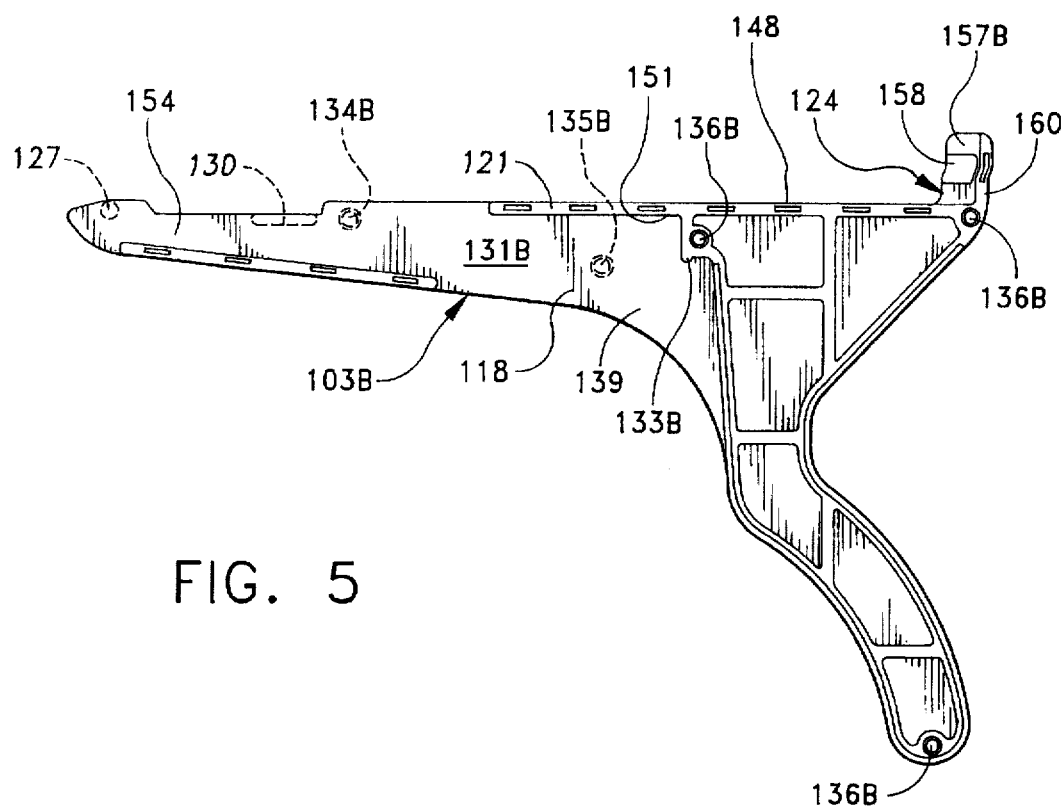
FIG. 5 is an internal side view of the right half of the body of the pistol grip subassembly.

Top wall 121 comprises a top surface 148 and a bottom surface 151 (FIGS. 4 and 5). An opening 154 is disposed distally of top wall 121, and communicates with chamber 118. Top wall 121 extends from retention channel 124 of body 103 to distal opening 154. Top surface 148 is adapted to provide a flat support surface for magazine subassembly 200, as will hereinafter be disclosed in further detail. Bottom surface 151 is adapted to provide a support for springs 112 and 113 (FIGS. 27, 28 and 33), as will hereinafter also be disclosed in further detail. Opening 154 extends from the distal end of top wall 121 to the distal tip of body 103 when the two body halves 103A, 103B are assembled together. Opening 154 is sized and shaped so as to accept a distal portion of lever 106, as will hereinafter be disclosed in further detail.

Magazine retention channel 124 projects upwardly from the proximalmost portion of top wall 121, and comprises two spaced-apart, opposing lateral side walls 157A, 157B and a back wall 160 (FIGS. 4 and 5). Walls 157A, 157B further include cut-outs 158 that are adapted to accept corresponding latches located on magazine 200, as will hereinafter be disclosed in further detail.

A magazine pivot tab 127 is disposed on each side of the distalmost portion of body 103 (FIGS. 3–6). Pivot tabs 127 project outwardly from body 103, and are sized and shaped to be received in a corresponding slot formed in magazine 200, as will hereinafter be disclosed in further detail.

A retainer slide tab 130 projects outwardly from each side of body 103, below opening 154 (FIGS. 3–6). Tabs 130 are sized and shaped to be engaged by a corresponding slide portion of magazine 200, as will hereinafter be disclosed in further detail.

Figure 7:
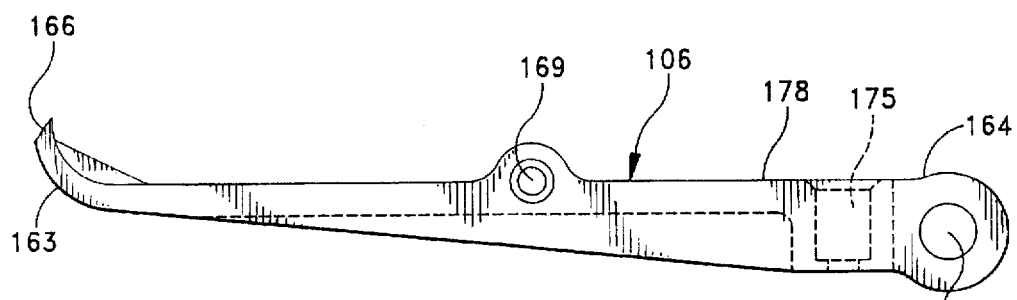
FIG. 7 is a side view of the lever.
Figure 8:
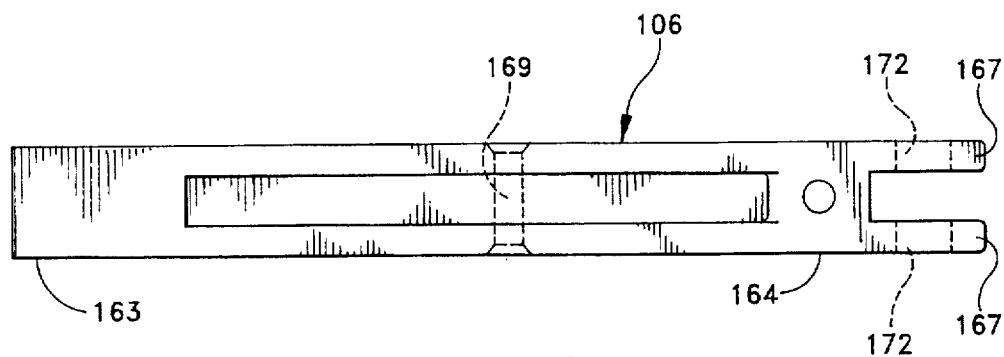
FIG. 8 is a bottom view of the lever shown in FIG. 7.

Referring next to FIGS. 7 and 8, lever 106 comprises an elongate beam having a distal end 163, a proximal end 164, and a central pivot hole 169. More particularly, distal end 163 includes a mandible 166 that is adapted to engage and grip a portion of a scalp clip 300 as will hereinafter be disclosed in further detail. Proximal end 164 is bifurcated into a pair of coupling flanges 167 that are sized and shaped so as to pivotally couple to a corresponding portion of trigger 109, as will hereinafter be disclosed in further detail. Each flange 167 includes an over-sized, elliptically-shaped transverse pivot hole 172 that is adapted to loosely receive coupling pin 173 (FIGS. 27, 28 and 33) so as to pivotally couple lever 106 to trigger 109 when pistol grip subassembly 100 is fully assembled. A recess 175 is disposed in top surface 178 of lever 106. Recess 175 is sized and shaped so as to accept and retain spring 112, as will hereinafter be disclosed in further detail.

Central pivot hole 169 is eccentrically disposed on a central portion of lever 106. Lever 106 is pivotally fixed within body 103 by means of lever pivot pin 137 which extends through lever pivot hole 169 (FIGS. 27, 28 and 33) and has its two ends fixed in body bores 134A, 134B.

Figure 9:
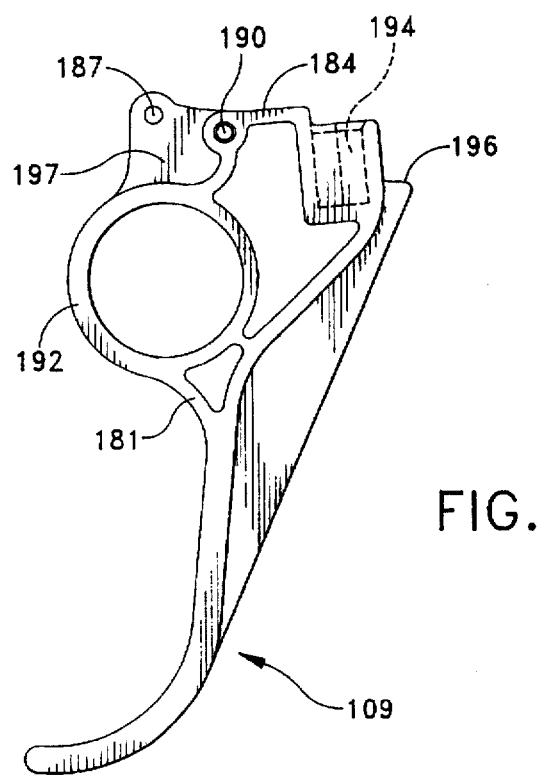
FIG. 9 is a side view of the trigger.
Figure 10:
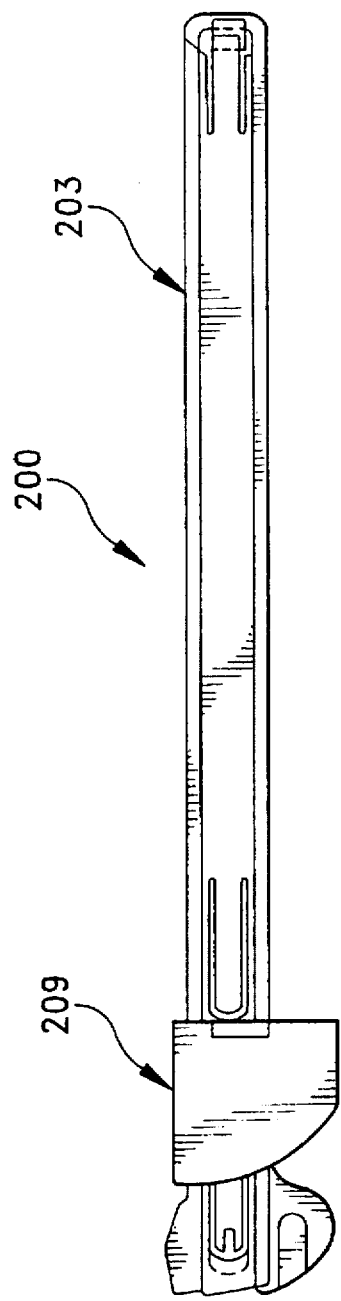
FIG. 10 is a side view of the clip applicator's magazine subassembly.

Looking next at FIG. 9, trigger 109 comprises a lower portion 181, an upper portion 184, a trigger pivot hole 187, and a body pivot hole 190. More particularly, lower portion 181 comprises a finger grip 192 that is adapted to be gripped by a human finger. Upper portion 184 includes a recess 194 that is adapted to accept and retain spring 113. A stop 196 projects outwardly from rear upper portion 184 and is adapted to engage shoulder 133 of body 103.

Still looking now at FIG. 9, trigger pivot hole 187 is disposed on a distal projection 197 of the trigger's upper portion 184. Distal projection 197 is adapted to be received between flanges 167 of lever 106 and fastened therebetween by coupling pin 173 (FIGS. 27, 28 and 33). Body pivot hole 190 is disposed in spaced relation to lever pivot hole 187, and is adapted to pivotally mount trigger 109 to body 103. More particularly, trigger 109 is pivotally attached to body 103 by means of trigger pivot pin 138 which extends through body pivot hole 190 (FIGS. 27, 28 and 33) and has its two ends fixed in bores 135A, 135B.

In a preferred embodiment, springs 112 and 113 (FIGS. 27, 28 and 33) comprise helical compression springs of the type well known in the art. Springs 112 and 113 are adapted to be received in recess 175 of lever 106 and recess 194 of trigger 109, respectively. Springs 112 and 113 are sized and shaped so as to be normally held in compression by bottom surface 151 of the body's top wall 121, as will hereinafter be disclosed in further detail. In a preferred embodiment, spring 112 has a lower spring constant than spring 113.

Figure 11:
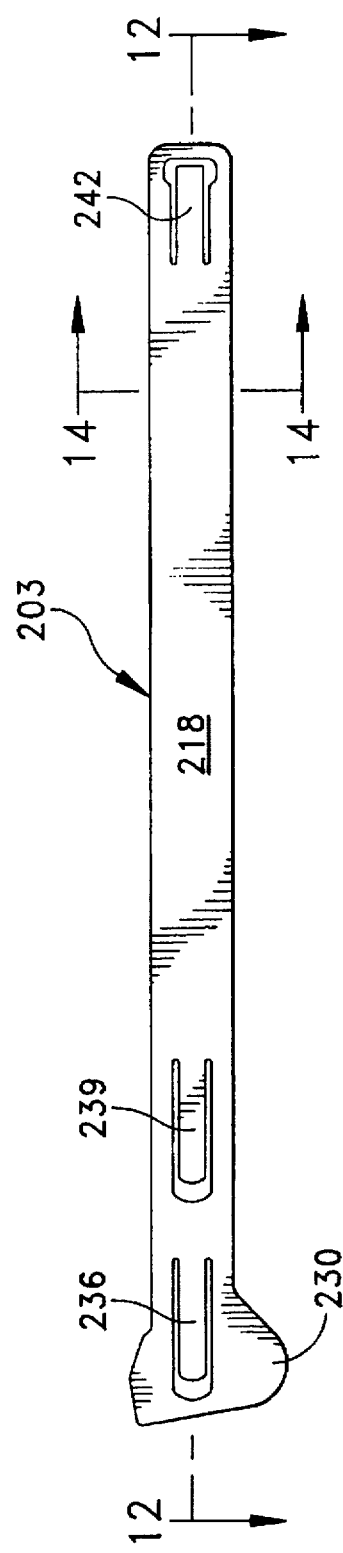
FIG. 11 is a side view of the magazine's tube.
Figure 12:
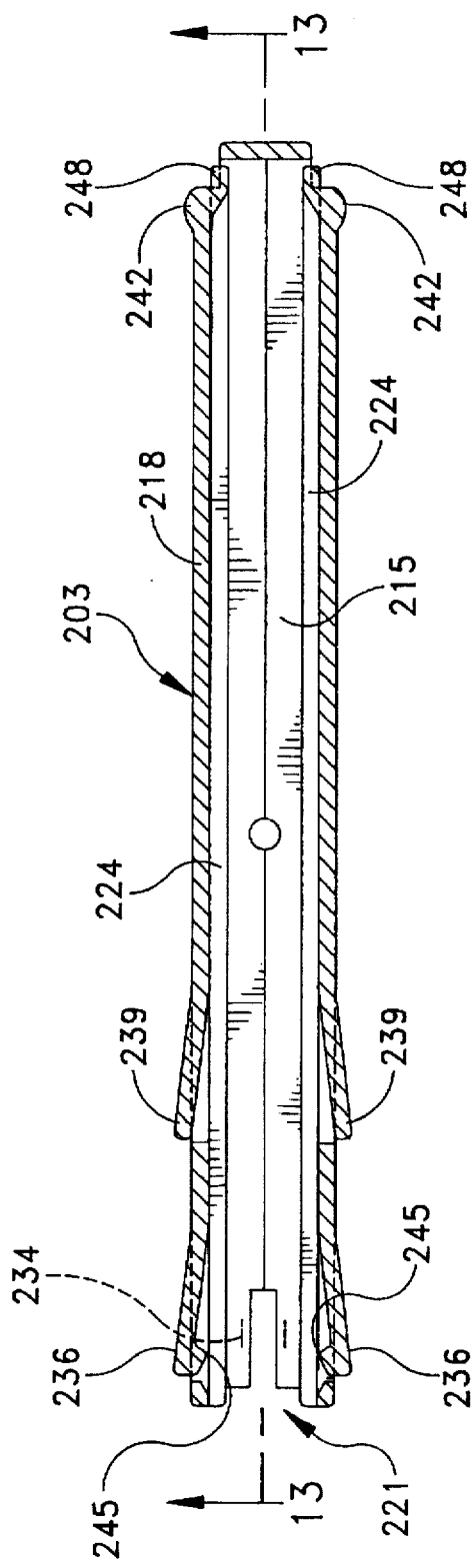
FIG. 12 is a cross-sectional view of the tube as taken along line 12—12 in FIG. 11.
Figure 13:
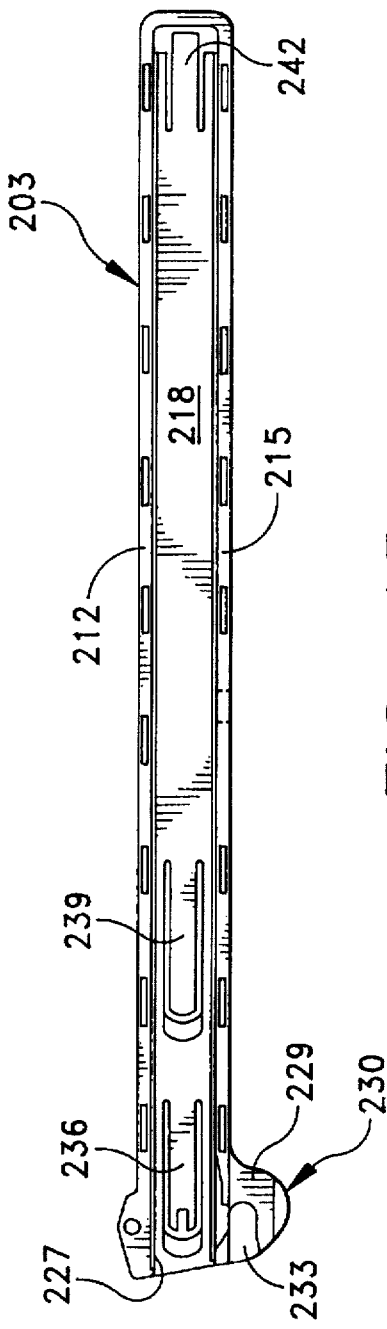
FIG. 13 is a side view of the right half of the tube shown in FIG. 11, as taken along line 13—13 in FIG. 12.
Figure 14:
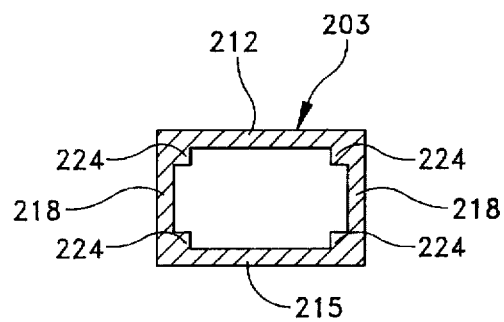
FIG. 14 is a cross-sectional view of the tube as taken along line 14—14 in FIG. 11.
Figure 15:
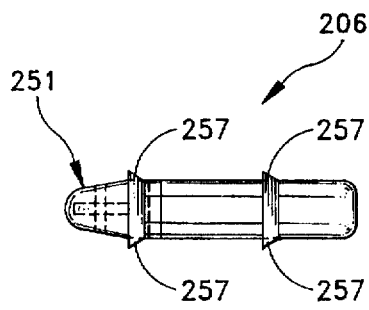
FIG. 15 is a side view of the magazine's pusher.
Figure 16:
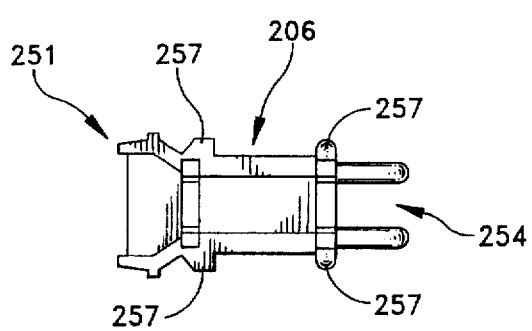
FIG. 16 is a top view of the pusher.
Figure 17:
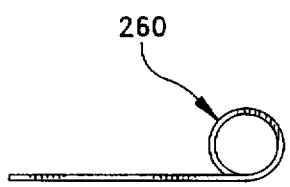
FIG. 17 is a side view of the magazine's coil spring.
Figure 18:
FIG. 18 is a top view of the coil spring shown in FIG. 17.
Figure 19:
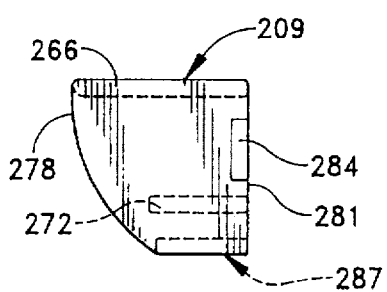
FIG. 19 is a side view of the magazine's retainer slide.
Figure 20:
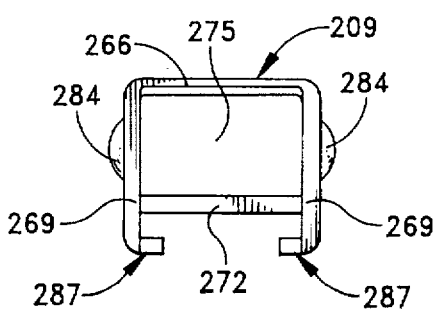
FIG. 20 is a front view of the retainer slide.

Referring now to FIGS. 10–18 and 29–31, magazine subassembly 200 generally comprises a tube 203 (FIGS. 10–14), a pusher 206 (FIGS. 15, 16, 29 and 30), and a retainer slide 209 (FIGS. 19 and 20). More particularly, tube 203 has a generally rectangular cross-section, and includes a top wall 212 (FIGS. 13 and 14), a bottom wall 215, two side walls 218 (FIGS. 11–14), an open end 221 (FIG. 12), and four spacers 224 formed at the apex of, and integral with, walls 212, 215 and 218 (FIGS. 12 and 14). Top wall 212 includes a lip 227 (FIG. 13) that is positioned adjacent to the tube's open end 221. Lip 227 projects downwardly into tube 203.

Bottom wall 215 is disposed in spaced-apart, confronting relation to top wall 212. Two guides 230 are positioned adjacent to open end 221 (FIGS. 11 and 13). Each guide 230 projects downwardly from the outer surface of bottom wall 215. The inner surface 229 of each guide 230 (FIG. 13) includes a slot 233. Slots 233 are disposed in spaced-apart, confronting relation to one another, and are sized and shaped so as to pivotally receive pivot tabs 127 when magazine subassembly 200 is assembled to pistol grip subassembly 100, as will hereinafter be disclosed in further detail. Bottom wall 215 (FIGS. 12 and 14) further includes a bottom recess 234 which is disposed adjacent to open end 221 of tube 203. Bottom recess 234 is sized and shaped so as to receive a portion of a coil spring associated with pusher 206, as will hereinafter be disclosed in further detail.

Side walls 218 each comprise a cantilevered clip latch 236 (FIGS. 11–13), a cantilevered retainer latch 239, and a cantilevered pistol grip latch 242. More particularly, each cantilevered clip latch 236 is positioned adjacent to, but spaced away from, open end 221 of tube 203. The free end of clip latch 236 is positioned closest to open end 221 and extends outwardly relative to side wall 218. A locking projection 245 (FIG. 12) is disposed at the free end of each clip latch 236 and projects inwardly, toward the interior of tube 203. Locking projections 245 are adapted to maintain scalp clips 300 in position within tube 203 when retainer slide 209 is placed in its distalmost position, as will hereinafter be disclosed in further detail.

A cantilevered retainer latch 239 is positioned behind the clip latch 236 on each side wall 218. The free end of retainer latch 239 is positioned closest to the fixed end of clip latch 236 and extends outwardly relative to side wall 218. Retainer latch 239 is adapted to hold retainer slide 209 aligned with (and in engagement with) clip latches 236 when the retainer slide 209 is placed in its distalmost position, as will hereinafter also be disclosed in further detail.

A cantilevered pistol grip latch 242 is positioned at the proximalmost end of each side wall 218. The free end of grip latch 242 is disposed adjacent to the proximalmost end of tube 203. A locking shoulder 248 (FIG. 12) projects outwardly from the free end of grip latch 242. Grip latches 242 are adapted to engage cut-outs 158 on the lateral walls 157 of magazine retention channel 124 (FIGS. 4 and 5) when magazine subassembly 200 is assembled to pistol grip subassembly 100, as will hereinafter be disclosed in further detail.

As shown in FIG. 14, one spacer 224 is positioned in each internal corner of tube 203. Each spacer 224 extends along substantially the entire internal length of tube 203. Each spacer 224 is sized and shaped so as to guide pusher 206 within tube 203, as will hereinafter be disclosed in further detail.

Referring now to FIGS. 15–18, the spring-biased pusher 206 is sized and shaped so as to fit within magazine tube 203. Spring-biased pusher 206 generally comprises a rounded front projection 251 (FIGS. 15 and 16), a rear recess 254, a plurality of guide tabs 257, and a coil spring 260 (FIGS. 17 and 18).

More particularly, rounded front projection 251 projects outwardly from the front end of pusher 206. Front projection 251 is sized and shaped so as to engage a corresponding portion of scalp clips 300. Rear recess 254 is disposed at the rear of pusher 206, and is adapted to receive and control the wound portion of coil spring 260. A plurality of guide tabs 257 project outwardly from both sides of, and from the top and bottom of, pusher 206. Guide tabs 257 are disposed in spaced-relation to one another, and are adapted to be slidingly received in the spaces defined between spacers 224 of tube 203. In a preferred embodiment, pusher 206 comprises four top guide tabs 257, four bottom guide tabs 257, and four side guide tabs 257, with the side guide tabs being arranged two to a side. Coil spring 260 includes a T-shaped free end 263 that is adapted to be received and held in the corresponding bottom recess 234 formed in bottom wall 215 of tube 203 (FIG. 12).

Referring now to FIGS. 19 and 20, retainer slide 209 comprises a generally tubular, rectangular configuration element having a top wall 266, two side walls 269, a bottom wall 272, and a central passageway 275. More particularly, retainer slide 209 is sized so as to slidingly receive magazine tube 203 within the retainer slide's central passageway 275. Side walls 269 each include a distal edge 278 and a proximal edge 281. Distal edge 278 is curved for ease of engagement with clip latch 236 and retainer latch 239 (FIG. 12), as will hereinafter be disclosed in further detail. Proximal edge 281 includes a pair of finger grips 284 that project outwardly from side walls 269. Two L-shaped locking projections 287 extend downwardly and inwardly from the lower edges of side walls 269. L-shaped locking projections 287 are oriented so as to extend underneath, and spaced away from, bottom wall 272. L-shaped locking projections 287 are disposed in spaced-apart, confronting relation, and are sized and shaped so as to engage slide tabs 130 of body 103, as will hereinafter be disclosed in further detail.

Figure 21:
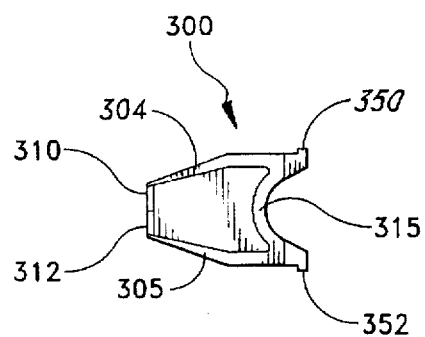
FIG. 21 is a side view of a preferred embodiment of the clip intended to be used in connection with the clip applicator of the present invention.
Figure 22:
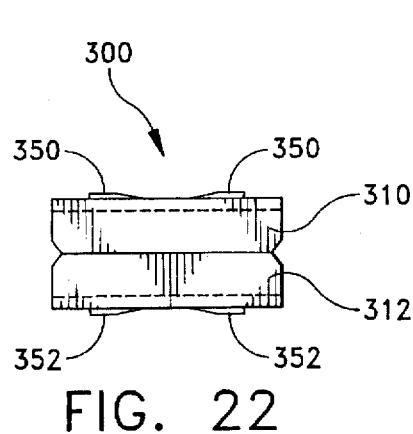
FIG. 22 is a front view of the clip shown in FIG. 21.
Figure 23:
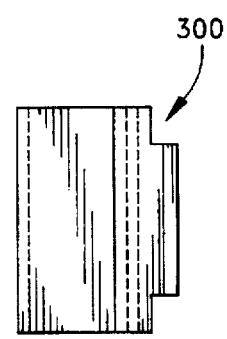
FIG. 23 is a top view of the clip shown in FIG. 21.
Figure 24:
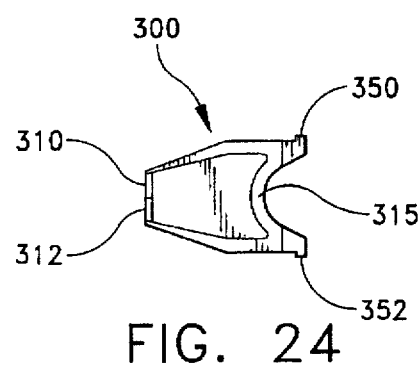
FIG. 24 is a side view of an alternative embodiment of the clip used in connection with the clip applicator of the present invention.
Figure 25:
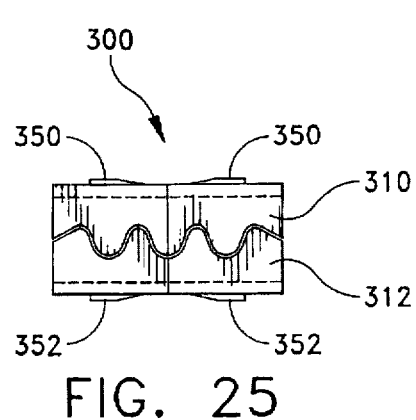
FIG. 25 is a front view of the clip shown in FIG. 24.
Figure 26:
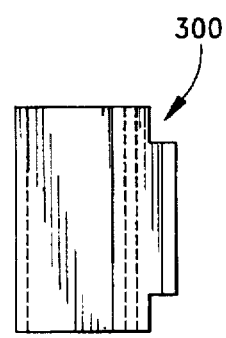
FIG. 26 is a top view of the clip shown in FIG. 24.

Referring next to FIGS. 21–26, clip applicator 5 is intended to be used with scalp clips 300. Scalp clips 300 essentially have a C-shaped cross-section, with a pair of legs 304 and 305 converging towards their free ends. Legs 304 and 305 have clamping jaws 310 and 312 at their free ends, and are connected with one another at their opposite ends by a bridge 315 which has a generally concave configuration. Scalp clips 300 are preferably produced in one piece from a suitable biocompatible polymer material, and are closed in their normal state, i.e. the two clamping jaws 310 and 312 are in engagement with one another. Clips 300 each include a pair of ears 350 and 352 which, when compressed towards one another, open the clamping jaws 310 and 312. FIGS. 21–23 illustrate one embodiment of scalp clip 300 in which clamping jaws 310 and 312 meet in a straight line. Alternatively, and as shown in FIGS. 24–26, clamping jaws 310 and 312 may also meet in a serpentine fashion to further facilitate the gripping of tissue at the incision site.

Clip applicator 5 is assembled by first assembling body 103, lever 106, and trigger 109 so as to form pistol grip subassembly 100. This is done by first mounting trigger 109 to one of the two body halves 103A, 103B. More particularly, trigger 109 is positioned against a side wall 131A or 131B so that the trigger's distal projection 197 (FIG. 9) faces the body's distal opening 154 (FIGS. 4 and 5) and the trigger's stop 196 faces the body's shoulder 133A or 133B, as appropriate. At the same time, trigger 109 is positioned against the body's side wall 131A or 131B so that the trigger's pivot hole 190 is in coaxial alignment with the body's bore 135A or 135B, as appropriate. Trigger 109 is then pivotally fastened to the body half by inserting trigger pivot pin 138 (FIGS. 27, 28 and 33) through the trigger's pivot hole 190 and into fixed engagement with body bore 135A or 135B, as appropriate.

Once trigger 109 is pivotally fastened to body half 103A or 103B, spring 113 is compressed and then placed into the trigger's recess 194 so that the spring extends between recess 194 and bottom surface 151 of top wall 121 (FIGS. 27, 28 and 33). As a result of this construction, trigger 109 is normally biased clockwise about pivot pin 138 by spring 113, when seen from the angle of view of FIG. 27.

Next, lever 106 is assembled to trigger 109 and the same body half 103A or 103B of pistol grip subassembly 100. More particularly, lever 106 is first positioned on the body half so that the lever's mandible 166 projects outwardly from the distalmost end of body opening 154. At the same time, the lever's central pivot hole 169 (FIG. 7) is disposed in coaxial alignment with body bore 134A or 134B, as appropriate (FIGS. 4 and 5), with the lever's two coupling flanges 167 (FIGS. 7 and 8) being disposed on either side of the trigger's distal projection 197 (FIGS. 27, 28 and 33). Next, lever pivot pin 137 is inserted through the lever's central pivot hole 169 and into fixed engagement within body bore 134A or 134B, as appropriate, so as to pivotally connect lever 106 to the body half.

Once lever 106 is pivotally fastened within the body half, spring 112 is compressed and then placed in the lever's recess 175 so that the spring extends between recess 175 and bottom surface 151 of top wall 121. As a result of this construction, lever 106 is normally biased clockwise about pivot pin 137 by spring 112, when seen from the angle of view of FIG. 27.

Once this operation is complete, the proximal end 164 of lever 106 is rotated toward body top wall 121 until the lever's pivot hole 172 is aligned with the trigger's pivot hole 187. Then coupling pivot pin 173 is inserted through the lever's pivot hole 172 and the trigger's pivot hole 187 so as to rotatably pin the proximal end 164 of lever 106 to the distal end 197 of trigger 109. It should be noted that the lever's pivot hole 172 is deliberately sized and shaped so as to provide a significant degree of clearance or "play" between the lever's pivot hole 172 and pivot pin 173. In a preferred embodiment, the diameter of pivot pin 173 is about half the diameter of the lever's oversized pivot hole 172.

It is to be appreciated that inasmuch as spring 112 has a lower spring constant than spring 113, lever 106 and trigger 109 will normally assume the position shown in FIG. 27 when these members are in their normal, "at rest" position. In particular, in this position, pivot pin 173 will be disposed in the uppermost portion of the lever's oversized transverse pivot hole 172.

At this point of assembly, the second body half is fastened to the first body half so as to complete the assembly of pistol grip subassembly 100.

It should be appreciated that once pistol grip subassembly 100 is fully assembled, spring 113 will normally maintain trigger 109 in its distalmost position relative to handle 115. This is because the spring constant of spring 113 is selected so as to be larger than the spring constant of spring 112. Also, in this position, pivot pin 173 will be pressing against the upper surface of the lever's oversized, elliptically-shaped pivot hole 172, whereby the lever's mandible 166 will be drawn downward relative to top surface 121 of body 103. Significantly, however, when pistol grip subassembly 100 is in this position, mandible 166 of lever 106 can still be forced even further downward against the force of spring 112 by a distance determined by the difference in the relative diameters of pivot pin 173 and lever pivot hole 172 (FIG. 33). However, it is to be appreciated that spring 112 will normally tend to bias lever 106 clockwise (when seen from the angle of view of FIG. 27), thereby keeping pivot pin 173 normally in contact with the upper inner surface of the lever's oversized transverse pivot hole 172 (FIG. 27).

Figure 29:
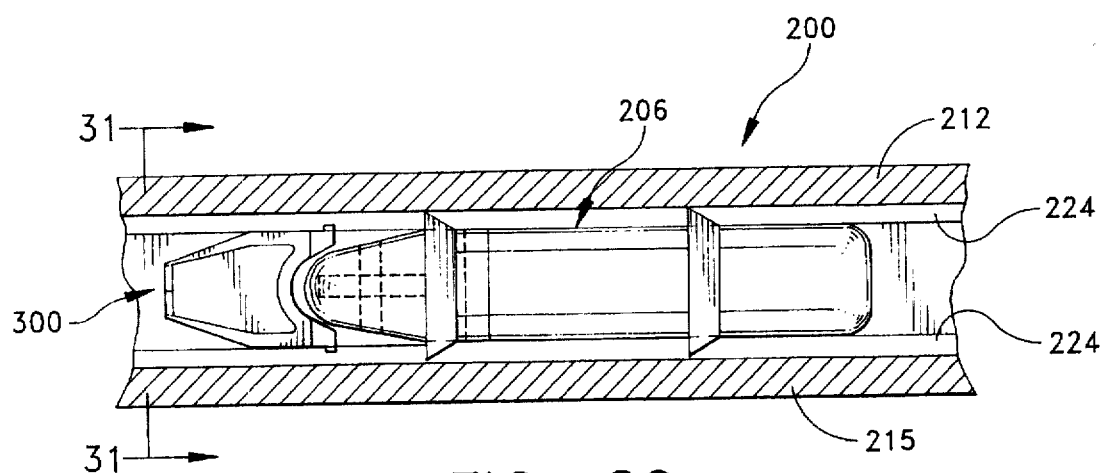
FIG. 29 is a side view, partially in section, showing the pusher and a clip disposed within the tube of the magazine subassembly.
Figure 30:
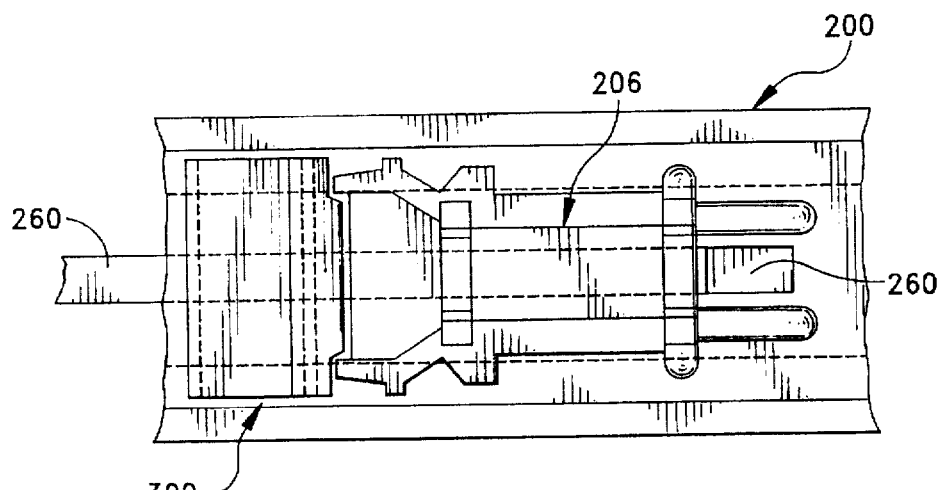
FIG. 30 is a top view of the pusher and clip shown in FIG. 29.
Figure 31:
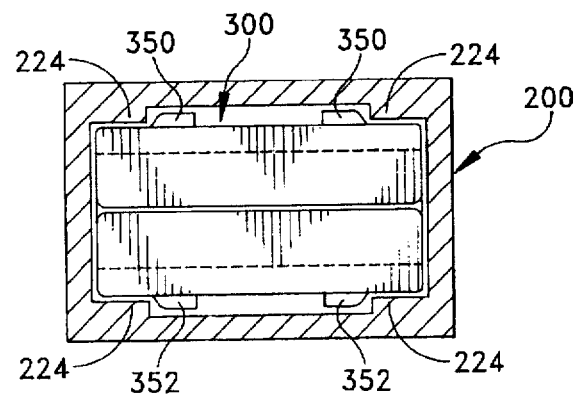
FIG. 31 is a cross-sectional view as taken along line 31—31 in FIG. 29.

Magazine subassembly 200 is assembled, and loaded with clips 300, as follows. Coil spring 260 is first positioned so that its T-shaped free end 263 (FIG. 18) is fastened in the tube's bottom recess 234 (FIG. 12). Next, pusher 206 is positioned within tube 203 so that the pusher's rounded front projection 251 is oriented towards the tube's open end 221 (FIGS. 29 and 30), with the coiled portion of coil spring 260 being disposed within the pusher's rear recess 254 (FIG. 30). Coil spring 260 is adapted so as to bias pusher 206 toward open end 221 of tube 203. When pusher 206 is in this position, the pusher's guide tabs 257 are disposed in the region between the tube's spacers 224 (FIGS. 29 and 30). In this way pusher guide tabs 257 and tube spacers 224 cooperate to maintain pusher 206 in a central position within tube 203. The tube's front lip 227 prevents pusher 227 from passing out the front end of tube 203.

Next, retainer slide 209 (FIGS. 19 and 20) is assembled onto the outer surface of tube 203. More particularly, retainer slide 209 is first oriented so that its distal edges 278 are positioned adjacent to the proximalmost ends of side walls 218. Retainer slide 209 is then slid distally over tube 203 so that tube 203 is positioned within the slide's central passageway 275. Retainer slide 209 is adapted to slide freely over the entire length of tube 203 between clip latches 236 and pistol grip latches 242 (FIG. 12). In a preferred method of assembly, retainer slide 209 is slid along tube 203 until the slide's distal edges 278 partially override the outer surfaces of retainer latches 239.

With retainer slide 209 positioned on tube 203 so as to partially override retainer latches 239, clips 300 may be inserted into tube 203. More particularly, a first clip 300 is oriented so that its concave bridge 315 is disposed in aligned, opposing relation to the rounded front projection 251 of retainer slide 209 (FIGS. 29 and 30). In this position, clip legs 304 and 305 extend distally from pusher 206. Clip 300 is then pressed into tube 203 by pushing proximally on the clip's clamping jaws 310 and 312 so as to force clip 300 (and hence pusher 206) rearward into tube 203. Once the first clip 300 is positioned within tube 203 so that jaws 310 and 312 are just level with tube open end 221, a second clip 300 is placed so that the second clip's concave bridge 315 nests on the jaws 310 and 312 of the first clip 300. The second clip 300 is then pushed proximally against the first clip 300, so that the second clip also enters tube 203. This procedure is repeated over and over again until the tube is fully loaded with a plurality of clips 300, with those clips being aligned one behind the other within the tube. In a preferred embodiment of the invention, tube 203 is adapted to hold at least 15 clips.

Once the final clip 300 has been inserted into tube 203, retainer slide 209 is slid distally along tube 203 so as to lock the last clip 300 in place within the magazine via clip latches 236. More particularly, as retainer slide 209 is urged distally along tube 203 by pressing on finger grips 284, the slide's distal edges 278 will engage the proximalmost ends of cantilevered clip latches 236. As retainer slide 209 is slid further distally along tube 203, clip latches 236 will be deflected inwardly, toward the interior of tube 203. As this occurs, the latches' locking projections 245 (FIG. 12) of clip latches 236 will engage the distalmost portion of the bridge 315 of the distalmost clip 300.

At the same time, as the retainer slide 209 locks clips 300 in place through its engagement with clip latches 236, the proximal edges 281 of the retainer slide will move past the distal ends of retainer latches 239. This will allow the free ends of retainer latches 239 to deflect outwardly to their normal, outwardly-projecting positions (FIG. 12). As a result, the free ends of retainer latches 239 will form stops for the slide's proximal edges 281 so as to hold retainer slide 209 in position over clip latches 236. As a result of this arrangement, clips 300 will be fixed in position within tube 203 so as to facilitate transfer and handling of the loaded magazine 200.

In order to release clips 300 from magazine 200, clip latches 236 must be released so that they are free to return to their normal, outboard position. This is done by moving retainer slide 209 proximally along tube 203. More particularly, when retainer slide 209 is to be moved proximally along tube 203, the free ends of retainer latches 239 are manually pressed inward toward the interior of tube 203. As this occurs, retainer slide 209 may be forced proximally so that it passes by the inwardly-deflected retainer latches 239. At the same time, as retainer slide 209 moves proximally along tube 203, it will disengage from clip latches 236, thereby permitting the clip latches to spring outboard once more and to withdraw their locking projections 245 from engagement with the bridge 315 of the leading scalp clip 300. In this way, scalp clips 300 will be free to move out of the distal end of tube 203 under the influence of the spring-biased pusher 206.

In order to use clip applicator 5 during a surgical procedure, a loaded magazine subassembly 200 is first assembled to the pistol grip subassembly 100. More particularly, the loaded magazine subassembly 200 (FIG. 10) is first oriented so that its open end 221 is positioned above the distalmost end of body 103. In this position, the magazine's guides 230 (FIGS. 11 and 13) are positioned above, and on either side of, the distalmost portion of body 103, adjacent to the body's distal opening 154. Magazine 200 is then moved toward body 103 so that the body's pivot tabs 127 (FIGS. 3 and 6) enter the slots 233 (FIGS. 11 and 13) on the inner surfaces 229 of guides 230. Once pivot tabs 127 have reached the end of slots 233, magazine 200 is rotated downward with respect to pistol grip subassembly 100 until the magazine's locking shoulders 248 (FIG. 12) of pistol grip latches 242 engage the top of the body's magazine retention channel 124 (FIGS. 4 and 5). As magazine 200 continues along its downward path toward top surface 148 of top wall 121, the body's lateral walls 157 cause pistol grip latches 242 to deflect inwardly until pistol grip latches 242 encounter the cut-outs 158 of lateral walls 157. Once this happens, the cantilevered grip latches 242 deflect outwardly once more, thereby locking magazine shoulders 248 in cut-outs 158. At this point the magazine's front lip 227 will sit in opposing relation to the pistol grip's mandible 166.

Figure 3:
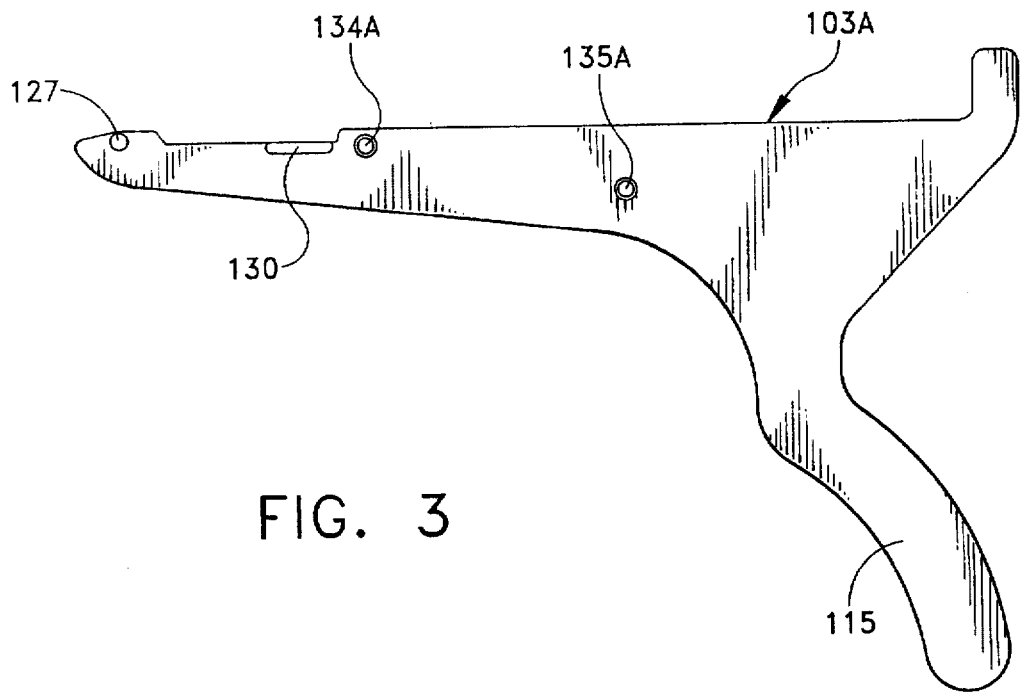
FIG. 3 is a left side view of the body of the pistol grip subassembly.
Figure 6:
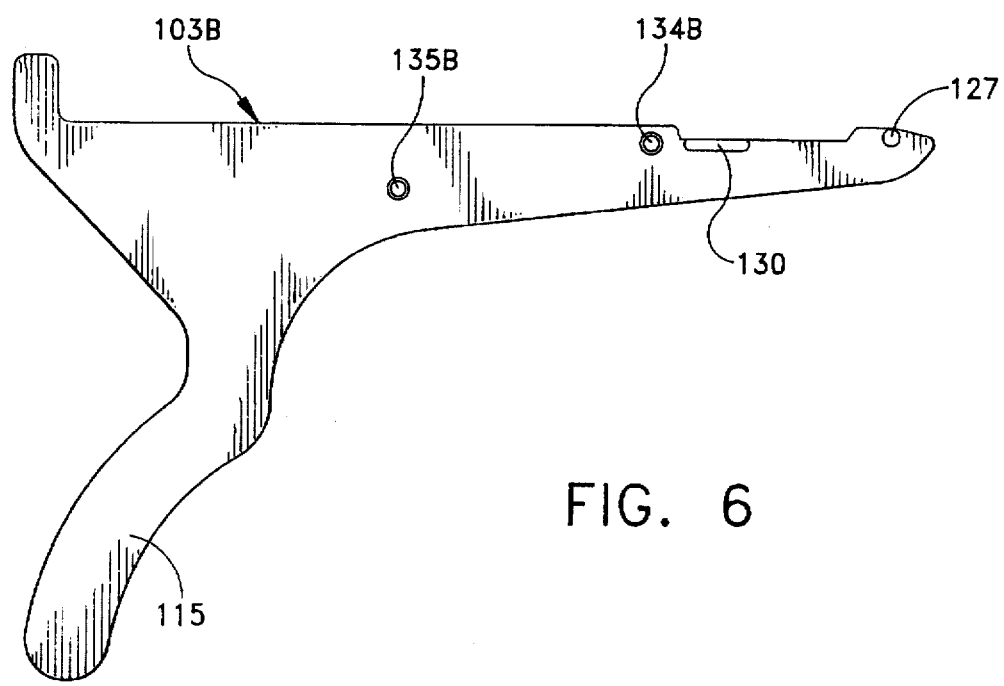
FIG. 6 is a right side view of the body of the pistol grip subassembly.
Figure 32:
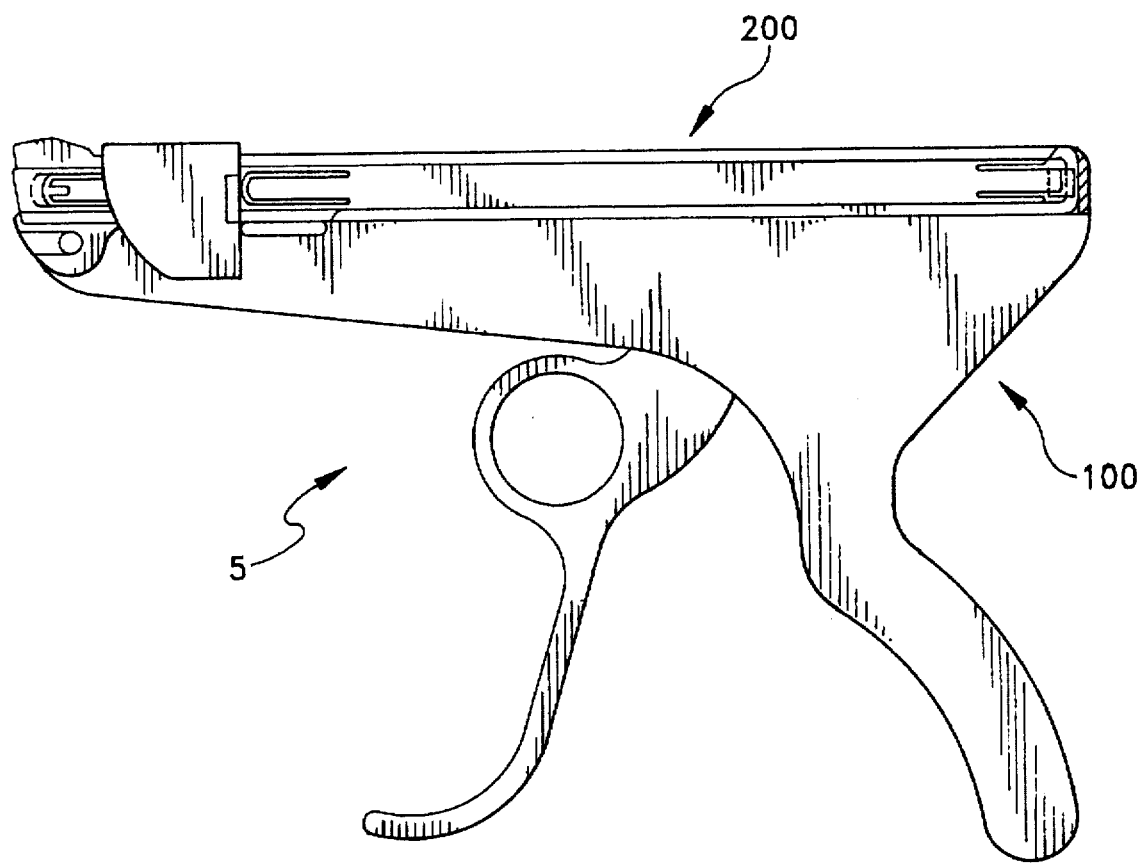
FIG. 32 is a side view of the clip applicator of the present invention, wherein the magazine subassembly has been joined to the pistol grip subassembly, but with the magazine's retainer slide being shown in its forward position.

Once magazine 200 is positioned on top surface 148 of top wall 121 (FIG. 32), the magazine's retainer latches 239 are pressed inwardly and retainer slide 209 is moved proximally until the slide's L-shaped locking projections 287 (FIG. 20) slidingly engage retainer slide tabs 130 (FIGS. 3 and 6). This will lock the magazine subassembly 200 to pistol grip subassembly 100 (FIG. 1). In this respect it is to be appreciated that once the slide's L-shaped locking projections 287 have fully engaged the body's retainer slide tabs 130, the slide's bottom wall 272 (FIG. 20) will engage the distalmost portion of the body's top wall 121, thus limiting further proximal movement of retainer slide 209 along magazine subassembly 200 and pistol grip subassembly 100. It is also to be appreciated that as retainer slide 209 is moved proximally from the position shown in FIG. 32 to the position shown in FIG. 1, the magazine's clip latches 236 will be released, thereby allowing the first clip 300 to protrude out of the open end of tube 203 (FIG. 1). However, this first clip 300 will be prevented from passing out the distal end of clip applicator 5 due to the engagement of clip ears 350 and 352 with magazine front lip 227 and lever mandible 166, respectively.

Clip applicator 5 is used to close tissue as follows. With a clip 300 positioned so as to be protruding out of the open end 221 of tube 203 (FIG. 1), clip applicator 5 is brought into close proximity with a wound flap at the incision site. Next, lower portion 181 of trigger 109 is squeezed so as to move the lower portion 181 of trigger 109 toward handle 115 of body 103. As this occurs, spring 113 is compressed between the bottom of trigger recess 194 and bottom surface 151 of top wall 121. At the same time, coupling pin 173 moves downwardly within body 103 under the influence of trigger 109.

Normally, in the absence of a clip 300 being positioned above mandible 166, downward movement of pivot pin 173 within body 103 would permit spring 112 to pivot lever 106 about pivot pin 137, with the proximal end of lever 106 following closely behind the moving pivot pin 173 so as to keep the top side of the lever's oversized pivot hole 172 in close engagement with the moving pivot pin 173. Thus, in the absence of a clip 300 being positioned above mandible 166, downward movement of pivot pin 173 merely frees lever 106 to rotate under the force of its own spring 112.

However, when a clip 300 is positioned above mandible 166 (i.e., in the case shown in FIG. 1), the resistance of clip 300 against the distal end of lever 106 exceeds the force of spring 112 against the proximal end of lever 106. As a result, when coupling pin 173 begins to move downwardly under the influence of trigger 109, the lever 106 initially remains at rest and coupling pin 173 simply passes across the diameter of the then-stationary lever's oversized pivot hole 172. When coupling pin 173 thereafter reaches the bottom end of the oversized pivot hole 172, coupling pin 173 solidly engages the proximal end of lever 106 and then causes the lever to begin to pivot about pin 137 (FIG. 28). In this way, the lever's mandible 166 moves upwardly so that the scalp clip's ears 350 and 352 are compressed between the magazine's stationary front lip 227 and the moving mandible 166. This in turn causes the scalp clip's clamping jaws 310 and 312 to be pivoted away from each other, about bridge 315, so as to open the scalp clip. The opened scalp clip is then positioned over the exposed end of a flap of tissue.

Once scalp clip 300 is appropriately positioned over the wound flap, trigger 109 is released so as to deploy the scalp clip on the wound flap. More particularly, as the lower portion 181 of trigger 109 is released, trigger portion 181 pivots away from handle 115 under the influence of spring 113. As this occurs, coupling pin 173 moves upward. As this occurs, lever 106 pivots, either under the influence of clip 300 pressing downward against mandible 166 or coupling pin 173 pressing upward against the top edge of oversized pivot hole 172, until lever 106 returns to the position shown in FIG. 27. As a result, the scalp clip's clamping jaws 310 and 312 move back toward one another, thus securely gripping the wound flap therebetween. Clip applicator 5 is then moved away from the secured clip so as to release the clip from opening 221 of tube 203.

In some situations, the deployed scalp clip may have trouble clearing its ears 350 and 352 from between magazine lip 227 and lever mandible 166. This is frequently the case where the clip is grasping relatively thin tissue and the deployed clip returns almost all the way back to its original configuration. In this case, uniquely, clip applicator 5 can be manipulated by hand against the deployed clip so as to cause the lever 106 to pivot slightly about its pivot pin 137, whereby mandible 166 will open further away from the magazine's lip 227 (FIG. 33). It is to be appreciated that this action can occur only with the clip applicator of the present invention, due to the uniquely oversized nature of the lever's pivot hole 172 relative to coupling pin 173.

After the deployed scalp clip 300 has been freed from the end of the clip applicator, the next clip 300 moves into position in opening 221 under the influence of spring-biased pusher 206.

Subsequent clips may thereafter be deployed by repeating the foregoing process.

The clip applicator of the present invention is also uniquely adapted to remove a scalp clip from the incision site at the conclusion of the surgical procedure. More particularly, once the magazine clip 200 has deployed all of its scalp clips, the surgeon may force the bridge 315 of a deployed scalp clip 300 back into position between lever mandible 166 and magazine lip 227 so as to reposition scalp clip 300 in opening 221 of tube 203. It will be appreciated that this is made possible due to the inherent "play" provided in the "at rest" lever 106. In other words, by deliberately providing a difference in diameter between oversized transverse pivot hole 172 and pivot pin 173, mandible 166 is capable of additional pivotal movement about central pivot hole 169 when lever 106 is in its "at rest" position. As a result, mandible 166 may be worked back onto the bridge 315 of a deployed scalp clip 300 with the clip applicator 5. Once in this position, trigger 109 may thereafter be squeezed once again so as to move lever mandible 166 toward magazine lip 227 once more so as to re-engage the ears 350 and 352 of the deployed clip and thereby expand jaws 310 and 312. The clip may then be withdrawn from the tissue and thereafter the surgical site. Finally, the removed clip may be released from the clip applicator 5 simply by relaxing trigger 109.

It is to be understood that the present invention is by no means limited to the particular construction herein disclosed and/or shown in the drawings, but also comprises any modifications or equivalents within the scope of the claims.

What is claimed is:

1. A clip applicator adapted to apply and remove C-shaped scalp clips wherein the C-shaped scalp clips each have two legs joined by a resilient bridge and including facing clamping jaws at their free ends and further wherein the bridge includes upper and lower ears adapted to urge the clamping jaws open in response to actuation of said clip applicator, said clip applicator comprising:

a body;

a trigger movably fastened to said body, said trigger having a trigger first position and a trigger second position relative to said body, wherein said trigger is normally pivotally biased in its said trigger first position by spring means, said trigger comprising (i) means for moving said trigger from its said trigger first position to its said trigger second position, and (ii) a lever-engaging portion;

a lever movably fastened to said body, said lever having a lever first position and a lever second position relative to said body, wherein said lever is normally pivotally biased in its said lever first position by spring means, said lever comprising an elongate beam having a clip-engaging portion disposed at a distal end thereof and a trigger-engaging portion disposed at a proximal end portion thereof, wherein said lever is movable from said lever first position to said lever second position in response to said trigger moving from said trigger first position to said trigger second position, and further wherein said trigger-engaging portion of said lever loosely engages said lever-engaging portion of said trigger such that said clip-engaging portion of said lever is movable relative to said body when said lever is in said lever first position;

a magazine releasably fastened to said body and adapted to store a plurality of clips such that the free ends of the clips rest against the bridge of an adjacent and preceding clip, and to serially dispense the clips from said magazine, said magazine having an open end, said magazine comprising a tube having side walls, means for orienting the clips within said tube such that the free ends of the clips point towards the magazine open end, means for releasably locking the clips within said tube, and a lip projecting into said open end, said lip being shaped so as to be selectively engageable with the upper ear of each of the clips as each clip moves toward said open end, and said magazine being positioned on said body such that said clip-engaging portion of said lever is engageable with the lower ear of each of the clips as each clip moves toward said open end, and further wherein said clip-engaging portion of said lever moves toward said lip when said trigger is moved from said trigger first position toward said trigger second position; and means for urging the clips toward said open end.

2. A clip applicator according to claim 1 wherein said trigger-engaging portion comprises an oversized elliptical hole extending through said proximal end portion of said lever.

3. A clip applicator according to claim 2 wherein said lever-engaging portion comprises a pin that is sized and shaped so as to be loosely received within said oversized elliptical hole.

4. A clip applicator according to claim 1 wherein said clip-engaging portion comprises a mandible.

5. A clip applicator according to claim 1 wherein said clip-engaging portion of said lever is adapted to move a sufficient distance relative to said body to be engageable with a deployed clip while said lever remains in said lever first position.

6. A clip applicator according to claim 1 wherein said means for releasably locking the clips within said tube comprise:

a first pair of cantilevered latches each disposed in opposing relation within a distal portion of said side walls of said tube, said first pair of latches each having a free end disposed adjacent to said open end and including a clip-engaging portion disposed at said free end thereof;

a second pair of cantilevered latches disposed in opposing relation with each other within said side walls of said tube, said second pair of latches each having a free end disposed adjacent to but proximal to said first pair of latches; and a retainer slide disposed in sliding relation to said magazine tube whereby when said retainer slide is moved over said free ends of said first pair of latches, said clip-engaging portions of said first pair of latches engage the bridge of at least one of said clips so as to prevent said clip from advancing toward said open end of said magazine, and further wherein said free ends of said second pair of latches engage a rear portion of said retainer slide so as to releasably lock said retainer slide in position.

7. A clip applicator according to claim 1 wherein said means for orienting said scalp clips within said tube comprise a plurality of spacers disposed within said tube, said spacers being located in relation to one another so as to be engageable with said clips along the peripheral edges of said clips, for preventing said clips from rotating within said tube.

8. A clip applicator according to claim 1 wherein said means for urging the scalp clips toward said open end comprise a spring-biased pusher adapted to be slidingly received within said tube, said pusher comprising a front end adapted to engage the bridge of the clips.

9. A method for applying and removing C-shaped scalp clips wherein the C-shaped scalp clips each have two legs joined by a resilient bridge and including facing clamping jaws at their free ends and further wherein the bridge includes upper and lower ears adapted to urge the clamping jaws open, said method comprising the steps of:

(a) providing a clip applicator comprising:
a body;
a trigger movably fastened to said body, said trigger having a trigger first position and a trigger second position relative to said body, wherein said trigger is normally pivotally biased in its said trigger first position by spring means, said trigger comprising (i) means for moving said trigger from its said trigger first position to its said trigger second position, and (ii) a lever-engaging portion;
a lever movably fastened to said body, said lever having a lever first position and a lever second position relative to said body, wherein said lever is normally pivotally biased in its said lever first position by spring means, said lever comprising an elongate beam having a clip-engaging portion disposed at a distal end thereof and a trigger-engaging portion disposed at a proximal end portion thereof, wherein said lever is movable from said lever first position to said lever second position in response to said trigger moving from said trigger first position to said trigger second position, and further wherein said trigger-engaging portion of said lever loosely engages said lever-engaging portion of said trigger such that said clip-engaging portion of said lever is movable relative to said body when said lever is in said lever first position;
a magazine releasably fastened to said body and adapted to store a plurality of clips such that the free ends of the clips rest against the bridge of an adjacent and preceding clip, and to serially dispense the clips from said magazine, said magazine having an open end, said magazine comprising a tube having side walls, means for orienting the clips within said tube such that the free ends of the clips point toward the magazine open end, means for releasably locking the clips within said tube, and a lip projecting into said open end, said lip being shaped so as to be selectively engageable with the upper ear of each of the clips as each clip moves toward said open end, and said magazine being positioned on said body such that said clip-engaging portion of said lever is engageable with the lower ear of each of the clips as each clip moves toward said open end, and further wherein said clip-engaging portion of said lever moves toward said lip when said trigger is moved from said trigger first position toward said trigger second position; and means for urging the clips toward said open end;

(b) positioning the ears of a first clip adjacent to said clip-engaging portion of said lever and said lip of said magazine;

(c) positioning said clamping jaws adjacent to a surgical incision site;

(d) moving said trigger from said trigger first position to said trigger second position so that said lever moves from said lever first position to said lever second position whereby said clip-engaging portion of said lever engages the lower ear and said lip engages the upper ear of the clip, thus causing the clamping jaws to spread apart;

(e) positioning said open clip so as to overlie tissue at said surgical incision site; and (f) moving said trigger from said trigger second position to said trigger first position so that said lever moves from said lever second position to said lever first position whereby said clip-engaging portion disengages from the ears of the scalp clip, thus allowing the clamping jaws to grip said tissue.

10. A method according to claim 9 further comprising the steps of:

(g) positioning said clip applicator so that said clip-engaging portion of said lever is adjacent to said ears of a previously-deployed scalp clip;

(h) pressing said clip-engaging portion of said lever against said lower ear of said deployed clip so that said clip-engaging portion of said lever moves relative to said body by an amount sufficient to re-capture said deployed clip between said clip-engaging portion of said lever and said lip of said magazine tube while at the same time said lever is maintained in said lever first position; and (i) moving said trigger from said trigger first position to said trigger second position so that said lever moves from said lever first position to said lever second position whereby said clip-engaging portion of said lever engages said lower ear of said released clip and said lip engages said upper ear of said released clip, thus causing said clamping jaws to once again spread apart so as to release said clip from said tissue.

* * * * *